US007689176B2

(12) United States Patent
Crivelli

(10) Patent No.: US 7,689,176 B2
(45) Date of Patent: Mar. 30, 2010

(54) TELEMETRY SYSTEM EMPLOYING DC BALANCED ENCODING

(75) Inventor: Rocco Crivelli, Bellinzona (CH)

(73) Assignee: Codman NeuroSciences Sárl, LeLocle (CH)

( * ) Notice: Subject to any disclaimer, the term of this patent is extended or adjusted under 35 U.S.C. 154(b) by 1196 days.

(21) Appl. No.: 11/073,444

(22) Filed: Mar. 7, 2005

(65) Prior Publication Data

US 2006/0199560 A1    Sep. 7, 2006

(51) Int. Cl.
  *H04B 1/034* (2006.01)
(52) U.S. Cl. .............. 455/100; 455/66.1; 455/90.1; 455/404.1
(58) Field of Classification Search ............ 455/100, 455/91, 95, 404.1, 66.1, 67.11, 90.1, 130, 455/215, 293, 311, 334, 336, 341; 340/870.1, 340/870.07, 870.16, 539.1, 572.4, 572.8, 340/572.12; 600/300–301, 309, 323, 331, 600/384, 492
  See application file for complete search history.

(56) References Cited

U.S. PATENT DOCUMENTS

| 4,681,111 | A | * | 7/1987 | Silvian ................. 607/59 |
| 5,193,539 | A |   | 3/1993 | Schulman et al. |
| 5,569,307 | A |   | 10/1996 | Schulman et al. |
| 5,644,286 | A |   | 7/1997 | Brosh et al. |
| 5,938,691 | A |   | 8/1999 | Schulman et al. |
| 6,052,635 | A |   | 4/2000 | Swart et al. |
| 6,073,050 | A | * | 6/2000 | Griffith .................. 607/57 |
| 7,256,695 | B2 | * | 8/2007 | Hamel et al. ............ 340/572.1 |
| 2003/0014090 | A1 | * | 1/2003 | Abrahamson ................ 607/60 |
| 2004/0062362 | A1 |   | 4/2004 | Matsuya |
| 2004/0125889 | A1 | * | 7/2004 | Cumeralto et al. .......... 375/303 |
| 2006/0007017 | A1 | * | 1/2006 | Mann et al. ............. 340/870.07 |
| 2006/0202859 | A1 | * | 9/2006 | Mastrototaro et al. .. 340/870.07 |
| 2007/0232936 | A1 | * | 10/2007 | Mann et al. ................ 600/486 |

OTHER PUBLICATIONS

"Implantable Selective Stimulator to Improve Bladder Voiding . . . ", Boyer et al., IEEE Transactions on Rehabilitation Engineering, vol. 8, No. 4, Dec. 2000, pp. 464-470.
"A Monolithic Miniaturized Programmable Implant For Neuomuscular Stimulation", Arabi & Sawan, Engineering in Medicine & Biology Society, vol. 2, Sep. 20, 1995, pp. 1131-1132.
"Implantable Active Telemetry System using Microcoils", Engineering in Medicine and Biology 27th Annual Conference, China, Sep. 1-4, 2005, pp. 7147-7150.

* cited by examiner

*Primary Examiner*—Pablo N Tran
(74) *Attorney, Agent, or Firm*—Cheryl F. Cohen, LLC

(57) ABSTRACT

A telemetry system including a first device having a processor that employs a DC balanced encoding scheme to generate a DC balanced encoded data signal, a modulator for modulating an RF carrier wave by the DC balanced encoded data signal and generating a DC balanced encoded RF modulated data signal including DC balanced RF energy. The DC balanced encoded RF modulated data signal transmitted by the first device is received by a second device. Since the RF energy received is DC balanced, drift in baseline voltage is eliminated irrespective of data transmission thereby improving the robustness of recovery of data by the second device. The second device may include a converter for converting the DC balanced RF energy extracted from the received DC balanced encoded RF modulated data signal to a substantially constant average induced voltage, irrespective of data being transmitted, for powering at least one component of the second device.

20 Claims, 4 Drawing Sheets

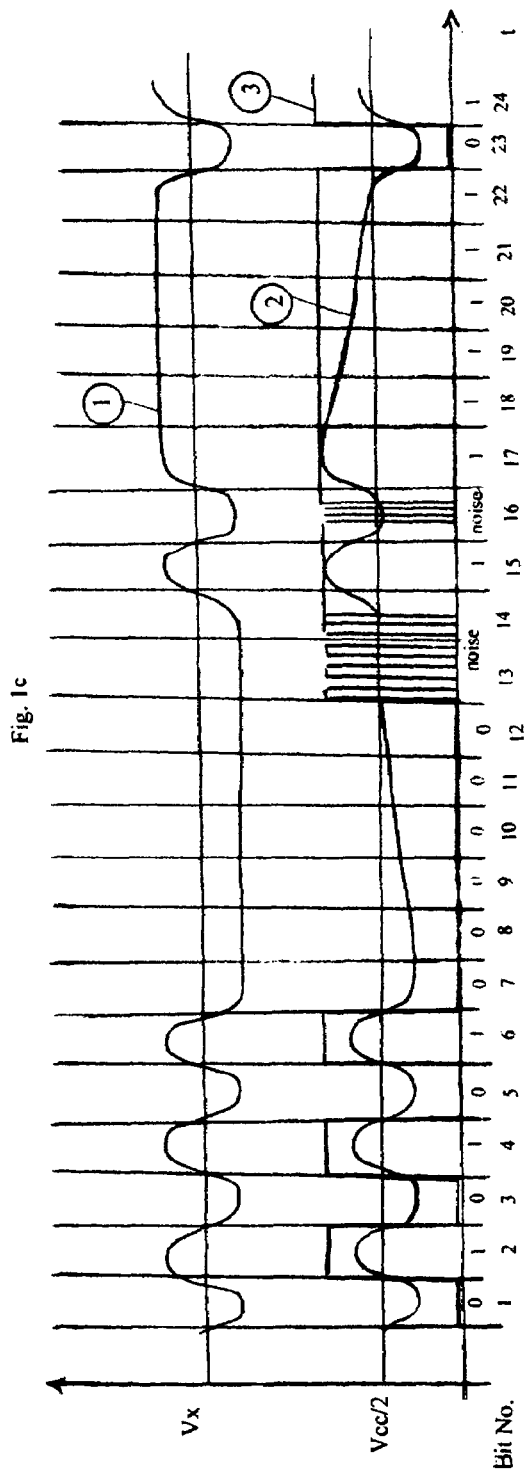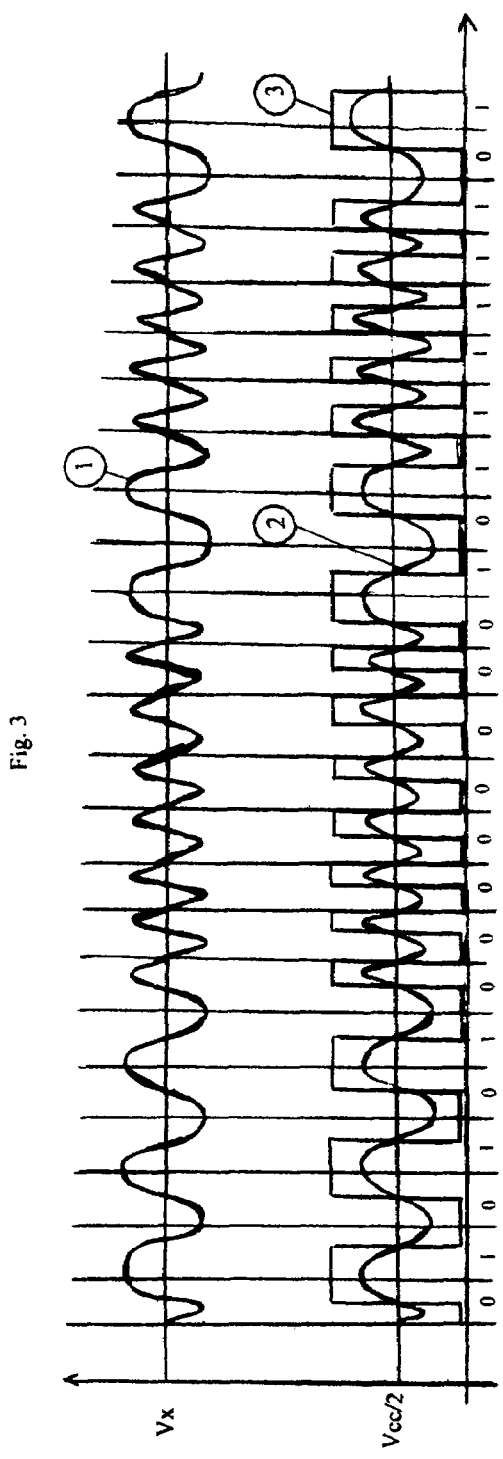

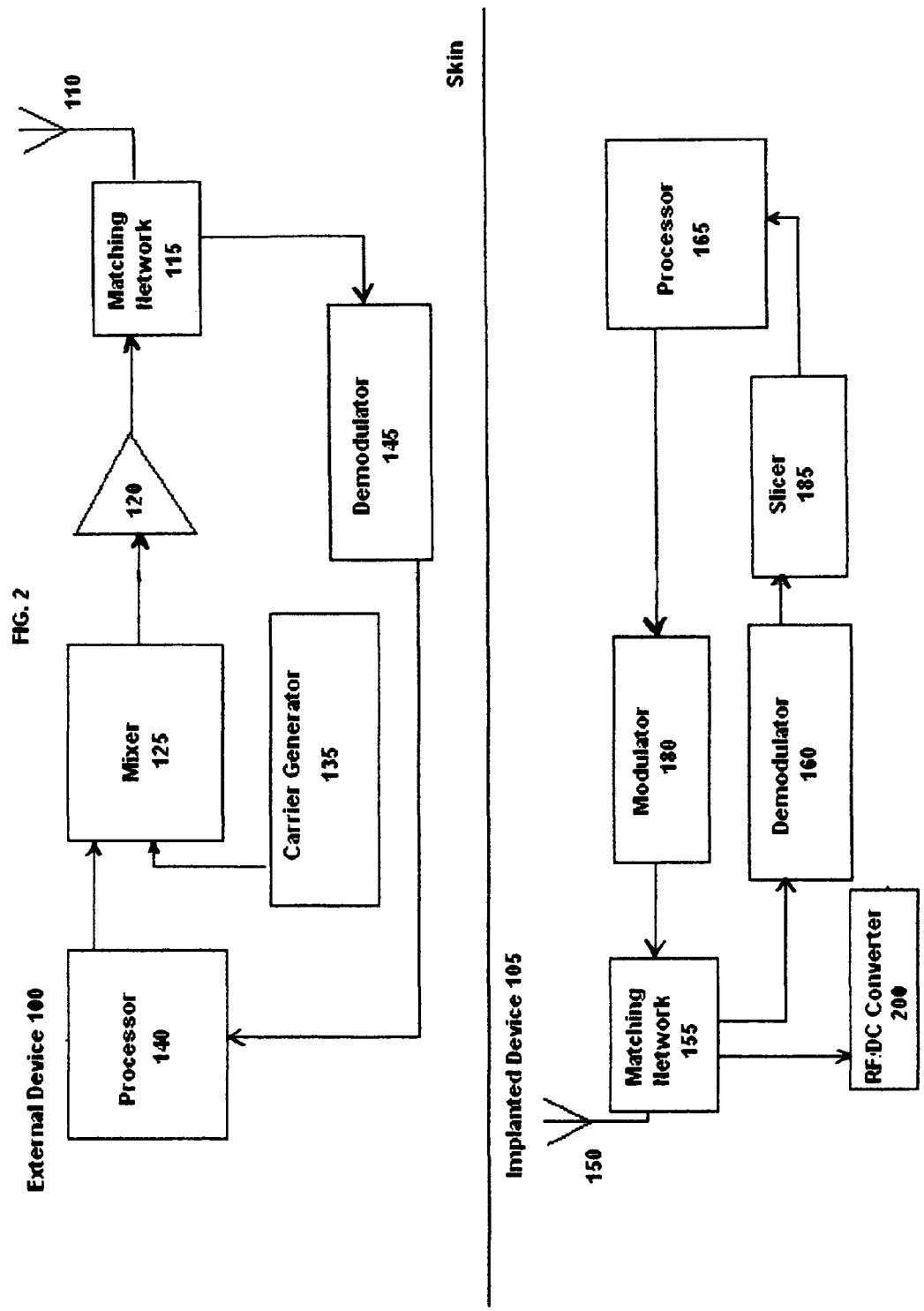

TELEMETRY SYSTEM EMPLOYING DC BALANCED ENCODING

BACKGROUND OF THE INVENTION

1. Field of the Invention

The present invention is directed to a telemetry system and, in particular, to a telemetry system in which an RF communication signal generated by a first device (e.g., an external device) is DC balanced encoded prior to transmission to a second device (e.g., an internal device) to optimize robustness of the wireless communication link and/or maintain a substantially constant average induced voltage in the second device irrespective of the data being transmitted.

2. Description of Related Art

In a variety of scientific, industrial, and medically related applications, it may be desirable to transfer energy and power (energy per unit time) across some type of boundary. For example, one or more devices that require power (e.g., electrical, mechanical, optical, and acoustic devices) may be located within the confines of a closed system, or "body," in which it may be difficult and/or undesirable to also include a substantial and/or long term source of power. The closed system or body may be delimited by various types of physical boundaries, and the system internal to the boundary may be living or inanimate, may perform a variety of functions, and may have a variety of operational and physical requirements and/or constraints. In some cases, such requirements and constraints may make the implementation of a substantial and/or long term "internal" power source for internally located devices problematic.

One common example of a closed system is the human body. In some medically related and scientific applications, a variety of prosthetic and other medical devices that require power may be surgically implanted within various portions of the body. Some examples of such devices include, but are not limited to, drug infusion pumps, pacemakers, defribllators, cochlear implants, sensors and stimulators.

Accordingly, in some medical implant applications, "transcutaneous energy transfer" (TET) devices are employed to transfer energy from outside the body to inside the body, to provide power to one or more implanted prostheses or devices from an external power source. One example of a conventional TET device is a transformer that includes a primary winding (or coil) external to the body and a secondary winding internal to the body. Both the primary and secondary windings generally are placed proximate to respective outer and inner layers of a patient's skin; hence, the term "transcutaneous" commonly refers to energy transfer "through the skin." Thus, the RF communication signal generated by the external device includes both a data stream signal and an RF energy signal. When received at the implantable medical device, the RF energy induces a voltage therein. This induced voltage may be utilized to power one or more components of the implantable medical device thereby reducing the consumption of energy drawn from an internal power supply that requires surgery to replace.

Heretofore in conventional telemetry systems, a standard binary encoding scheme (i.e., a low level state for "0"s and a high level state for "1"s) and amplitude shift keying (ASK) modulation have been employed, wherein full power (maximum level) is emitted from the external device when transmitting a "1" while reduced energy (minimum level) is emitted from the external device when transmitting a "0". Accordingly, the amount of power received by the implantable medical device fluctuates, that is, a minimum level of energy is received when transmitting a "0" bit while a maximum level of energy is received during transmission of a "1" bit. A string of successive "1"s produces a relatively high level of power that may potentially exceed the maximum threshold for proper operation of the implantable medical device. In the case in which the external device transmits a string of successive "0"s then the internal device receives a reduced energy level. If the telemetry system is a passive telemetry system whereby some of the power or energy necessary to operate at least one component in the implantable medical device is provided by the passive power source, it is possible that an insufficient amount of energy may be received by the implantable medical device if the data stream includes a relatively long duration of successive "0" bits. For instance, if the data stream is "1000000001" then during the eight successive "0" bits the implantable medical device receives a reduced energy level. It is desirable in a passive telemetry system to maintain a substantially constant average energy level induced in the implantable medical device irrespective of the data being transmitted.

Another problem associated with using a binary encoding scheme is that the received power levels in the implantable medical device associated with the high and low bits differs based on the distance separation between the antennas of the external and internal devices. As a matter of convenience the external device is typically portable relative to that of the implantable medical device. Therefore, variations in the distance separation between the coils of the external and internal devices relative to one another will cause fluctuations in the power level received by the implantable medical device for the associated bits. In general there is an inverse relationship between the coil separation distance and the power level of the bit received by the implantable medical device. That is, the smaller the distance separation between the two coils relative to one another the higher the bit power level received by the implantable medical device. As the separation distance between coils increases the received bit power level decreases. By way of example, when the distance separation between the coils of the respective external and internal devices is relatively small then a "1" bit may be received at a power level of 5 while a "0" bit is received at a power level of 3. A result of a difference of 2 is obtained between the high and low bit power levels. On the other hand, at a relatively large separation distance between the coils of the respective external and internal device a "1" bit may be received at the implantable medical device at a power level of 3 while the "0" bit may be received with a power level of 2. Under this second set of exemplary conditions, the difference in power level between the high and low bits is 1. Accordingly, the difference in high and low bit power levels varies depending on the distance separation of the external and internal coils. The farther the distance separation between the coils the smaller the difference in received power levels between the high and low bits, whereas the shorter the distance separation the greater the difference in received power levels between the high and low bits.

Variations in the difference in power level of the associated high and low bits based on the coupling distance between the coils of the external and implantable medical devices complicates recovery of the original data signal. A conventional wireless communication receiver as found in an internal device typically includes a demodulator (e.g., a low pass filter (LFP)) that extracts an envelope from the modulated RF communication signal. The amplitude (DC component) of the envelope varies depending on the distance separation between the antenna coils of the external and internal devices. Accordingly, the envelope extracted from the modulated RF signal must be properly centered prior to passing through the slicer in order to ensure that the reference voltage will slice the envelope symmetrically. Specifically, the envelope (Vin) extracted by the demodulator is received as input to a data slicer 185, as shown in FIG. 1a, that (i) centers the envelope using a capacitor 190 around a reference voltage (e.g., an average DC voltage level (Vcc/2), wherein Vcc is the power supply voltage of a processor), (ii) slices the envelope by the reference voltage (e.g., Vcc/2) using a comparator 195 to recover the digital data signal, and (iii) reshapes the digital data signal prior to being transmitted to a processor.

FIG. 1b shows, for an ideal data bit stream of alternating "1"s and "0"s, three exemplary waveforms representative of different stages in a conventional RF wireless communication system including an external device that employs a binary encoding scheme in wireless communication with an internal device. Waveform #1 represents an envelope extracted by the demodulator from a conventional binary encoded RF modulated signal for the exemplary ideal data bit stream. Thereafter, the extracted envelope is centered (as represented by waveform #2) about the reference voltage (e.g., Vcc/2) after passing through the capacitor 190. The centered envelope is symmetrically sliced and the digital signal output (as represented by waveform #3) is unaffected by the distance separation between the coils of the external and internal devices. Under these ideal conditions (i.e., a data stream comprising alternating bits) the envelope is properly centered and symmetrically sliced. Thus, the use of a conventional binary encoding scheme under these ideal conditions does not have any negative effect on the recovery of the original data stream (as represented by waveform #3).

However, a typical data stream rarely comprises exclusively alternating bits more often including strings of varying lengths of the same successive bits. When using a conventional binary encoding scheme a relatively long string of the same successive bit (e.g., "1"s or "0"s) behaves like a DC voltage that is blocked by the capacitor 190. As a result of the DC blocking the envelope will not be properly centered and thus not slice symmetrically whereby some data bits may be missed by the slicer during recovery from the RF modulated signal. FIG. 1c is an alternative scenario of a more practical data bit stream "01010100000000101111111101". In the exemplary data stream, the period of eight successive "0"s behaves as a constant DC voltage that is blocked by the capacitor 190 causing the output of the capacitor 190 (represented by waveform #2) to approach and eventually equal Vcc/2. When the voltage of the envelope output from the capacitor 190 equals Vcc/2 (as during the $13^{th}$ and $14^{th}$ bits) then both inputs to the comparator 195 are the same. Under these conditions the comparator output is a noise signal that toggles undesirably based on the noise levels associated with each input to the comparator. Accordingly, the exemplary reshaped and sliced digital data signal output (as represented by waveform #3) is unable to recover the original data stream during the $13^{th}$ and $14^{th}$ bits. This example illustrates that a string of the same successive bits may impact the recovery of one or more of those bits.

In addition, the string of successive bits may result in the drift of the baseline voltage which may effect the recovery of subsequent bits in the data stream. As clearly represented during the alternating first six bits of the data stream in which the envelope is properly centered about the baseline voltage Vcc/2, a transition in bits (e.g., from "0" to "1", or from "1" to "0") results in a substantially constant voltage increase/decrease after the capacitor of approximately Vcc/2. As mentioned above, after the string of 8 successive "0" bits, the baseline voltage is approximately Vcc/2. Thereafter, during the transition from "0" to "1" between the $14^{th}$ and $15^{th}$ bits the voltage increases from Vcc/2+Vcc/2. Next the data stream transitions between the $15^{th}$ and $16^{th}$ bits from a "1" to a "0" whereby the voltage decreases by Vcc/2 and returns to the baseline voltage of Vcc/2=(Vcc/2+Vcc/2)−Vcc/2, which once again due to the fact that both inputs to the comparator are the same generates noise during the $16^{th}$ bit. This generation of noise during the $16^{th}$ bit is therefore a result of drift of the baseline voltage which affects subsequent bits until a properly centered baseline voltage is realized.

A similar effect to that of the string of successive "0"s is encountered during the string of six successive "1"s which also behaves as a constant DC voltage that is blocked by the capacitor 190. The envelope output from the capacitor (represented by waveform #2) once again approaches Vcc/2. However, in the case of the string of six successive "1"s the $23^{rd}$ bit toggles to "0" before the centered envelope (as represented by waveform #2) reaches Vcc/2.

It is therefore desirable to develop an improved passive telemetry system that overcomes the aforementioned problems by inducing a substantially constant power in the implantable medical device regardless of the bit stream being transmitted while facilitating recovery of the original data signal by ensuring a zero DC offset.

SUMMARY OF THE INVENTION

The present invention is directed to an improved telemetry system including an external device having an active emitter and an internal device, wherein the RF communication signal is DC balanced encoded prior to transmission from the external device to the internal device.

Another aspect of the present invention relates to an improved telemetry system that ensures a substantially constant power is induced in the internal device irrespective of the data stream being transmitted.

Still another aspect of the present invention relates to an improved passive telemetry system wherein the RF modulated signal has a zero DC offset thereby improving the robustness of transmission.

A telemetry system in accordance with the present invention includes a first device (e.g., an external device) in RF communication with a second device (e.g., an internal device). The first device includes a processor that employs a DC balanced encoding scheme to generate a DC balanced encoded data signal, a carrier generator for generating an RF carrier wave, a modulator for modulating the RF carrier wave by the DC balanced encoded data signal and generating a DC balanced encoded RF modulated data signal including DC balanced RF energy, and a transmitter for wirelessly transmitting the DC balanced encoded RF modulated data signal. An antenna, coil or winding of the second device receives the DC balanced encoded RF modulated data signal transmitted by the first device and recovers the original data signal. Since the RF energy is DC balanced as a result of the RF carrier wave being modulated by the DC balanced encoded data signal, drift in baseline voltage is eliminated irrespective of data transmission thereby improving recovery of data by the second device. In an alternative embodiment wherein the telemetry system is a passive telemetry system (i.e., a telemetry system in which the second device utilizes the DC balanced RF energy extracted from the DC balanced encoded RF modulated data signal to power at least one component thereof) then the use of the DC balanced encoding scheme advantageously maintains a substantially constant average induced voltage in the second device.

The invention also relates to a method of RF communication using the telemetry system described above. A DC balanced encoding scheme is applied to a data signal to produce a DC balanced encoded data signal. Then a generated RF carrier wave is modulated by the DC balanced encoded data signal to produce a DC balanced encoded RF modulated data signal including DC balanced RF energy. The DC balanced encoded RF modulated data signal is transmitted by the first device and received at the second device.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIG. 1b is a graphical representation for an exemplary data stream comprising alternating bits of "1"s and "0"s of: (i) an envelope waveform extracted by the demodulator from the received binary encoded RF modulated signal; (ii) the centered envelope waveform output from the capacitor; and (iii) the reshaped and sliced digital data output of the slicer, wherein the numbers identifying each waveform correspond to those at respective stages in the circuit shown in FIG. 1a;

FIG. 1c is a graphical representation for an exemplary data stream "01010100000001011111101" of: (i) an enveloped extracted by the demodulator from the received binary encoded RF modulated signal; (ii) the envelope output from the capacitor; and (iii) the reshaped and sliced digital data output of the slicer, wherein the numbers identifying each waveform correspond to those at respective points in the circuit shown in FIG. 1a;

FIG. 2 is an exemplary passive telemetry system in accordance with the present invention including an external device in wireless communication with an implantable medical device wherein the external device Manchester encodes the data prior to transmission to the internal device; and FIG. 3 is a graphical representation for an exemplary data stream "01011000000001011111101" of: (i) an enveloped extracted by the demodulator from the received DC balanced encoded RF modulated signal; (ii) the centered envelope output from the capacitor; and (iii) the reshaped and sliced digital data output of the slicer in FIG. 2.

DETAILED DESCRIPTION OF THE INVENTION

Figure 1A:
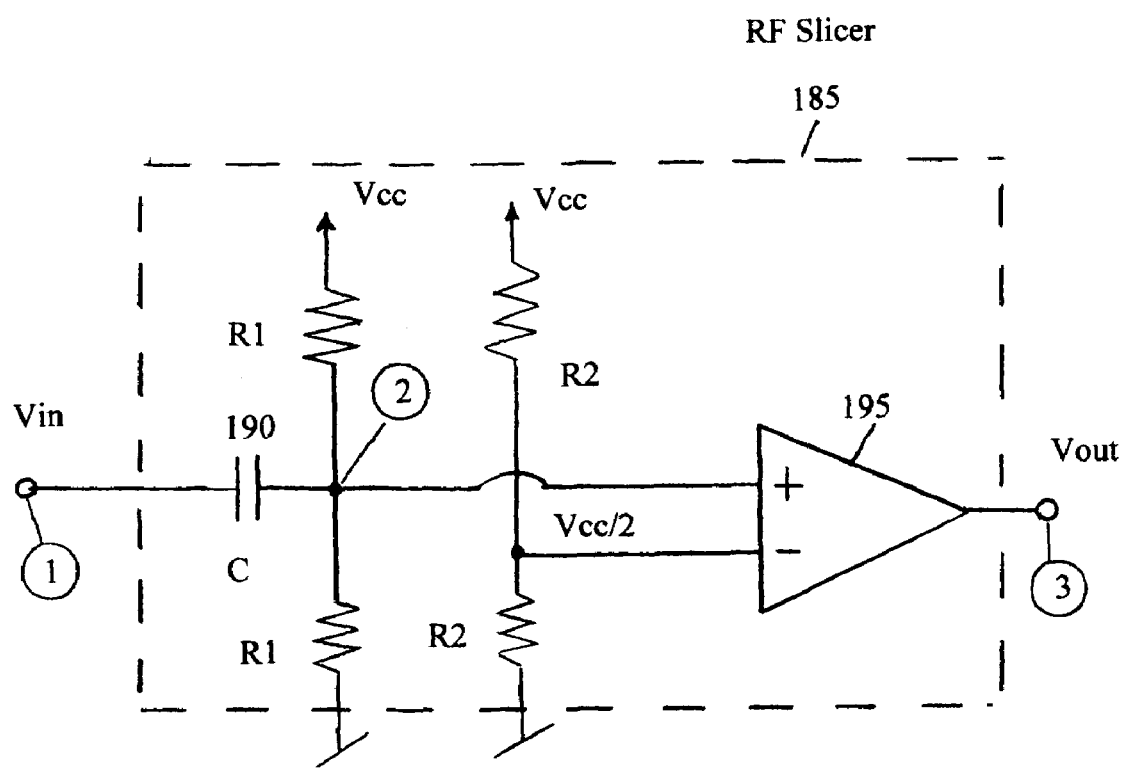
FIG. 1a is a prior art slicer employed in conventional wireless communication receivers.
Figure 1B:
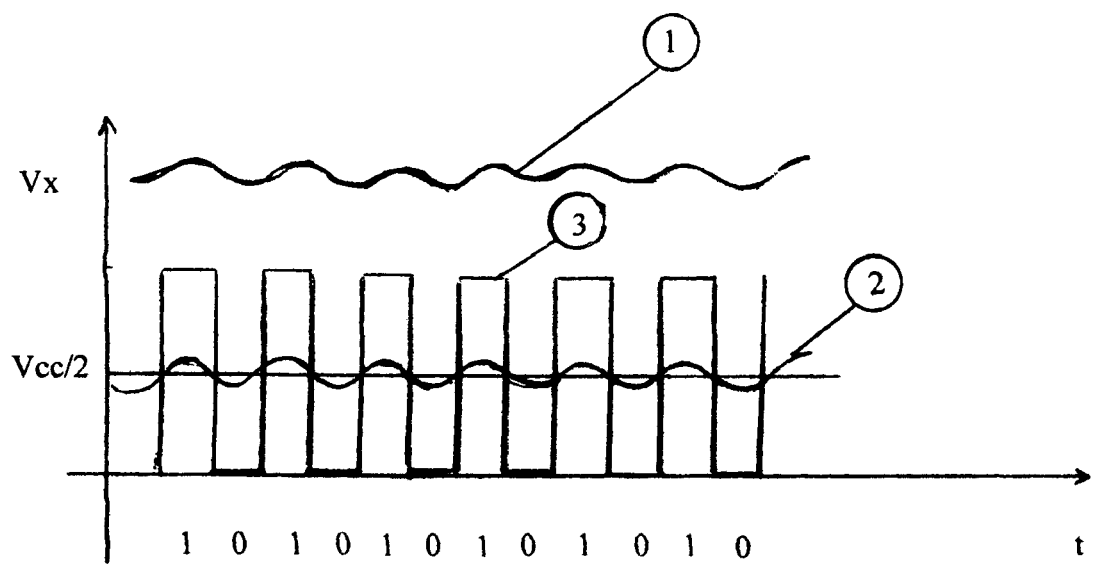

FIG. 2 represents an exemplary passive telemetry system (e.g., a transcutaneous energy transfer (TET) system) in accordance with the present invention including an external device 100 such as a processor, personal computer, or personal digital assistant (PDA) in telemetric communication with an internal device 105 such as an implantable medical device, for example, a drug delivery pump, stimulator or sensor. During communication a DC balanced encoded RF modulated data signal is generated by the external device and transmitted wirelessly to the implantable medical device. The transmitted DC encoded RF modulated data signal includes RF energy. At the implantable medical device 105, the received RF energy induces a voltage therein that is used to power at least one component of the implantable medical device.

External device 100 includes a processor or controller 140 that employs a DC balanced encoding scheme to produce a DC balanced encoded data signal which is received as one input to a mixer 125. A second input to the mixer 125 is connected to a carrier generator 135 that generates an RF carrier wave. In a preferred embodiment, the carrier frequency selected is approximately 13.56 MHz. The DC balanced encoded RF modulated data signal output from mixer 125 is amplified in block 120 followed by matching network 115 and transmitted by a primary antenna, winding or coil 110 to the internal device 105. In an alternative embodiment, amplifier block 120 may be arranged as an input to mixer 125.

As previously mentioned, the DC balanced encoded RF modulated data signal generated by the external device 100 includes both a DC encoded RF modulated data stream signal and a DC balanced RF energy signal (as a result of the modulation of the RF carrier wave by the DC balanced encoded data signal). On the implant side, the DC balanced encoded RF modulated data signal is received by a secondary antenna, winding or coil 150 and, in particular, the DC balanced RF energy component thereof induces a voltage therein. Thereafter, the DC balanced encoded RF modulated data signal passes through matching network 155.

A first output of the matching network 155 is electrically connected to an RF/DC converter 200 which extracts the DC balanced RF energy from the received DC balanced encoded RF modulated data signal and converts it to an analog DC induced voltage signal. The induced voltage is preferably used to power one or more components of the implantable medical device 105 thereby reducing the consumption of energy drawn from an internal power supply that requires surgery to replace.

A second output of the matching network 155 is coupled to demodulator 160 to extract an envelope from the DC balanced encoded RF modulated data signal. The envelope is then centered about a reference voltage, reshaped and sliced using a slicer 185 before recovering the digital data signal from the RF modulated signal. The recovered digital data signal is finally transmitted to a processor or controller 165. After receiving the DC balanced encoded RF modulated data signal from the external device 100, on the implant device side processor 165 in response thereto generates a responsive data signal which is modulated in block 180 prior to being received by the matching network 155. The RF modulated responsive data signal is then transmitted via the secondary antenna, winding or coil 150 to the external device 100. On the external device side, the transmitted RF modulated responsive data signal is received by primary antenna, winding or coil 100 and passed through the matching network 115 prior to being demodulated in block 145. The recovered data signal output from the demodulator is received as input by the processor 140.

Heretofore, conventional passive telemetry systems employed a standard binary encoding scheme and ASK modulation prior to transmitting a communication signal from the external device to the implantable medical device. Since standard binary encoding schemes employ high and low bit levels the amount of power induced in the implantable medical device undesirably fluctuates depending on the bits comprising the specific data stream being transmitted. If the data stream comprises a plurality of successive "1"s then an elevated power level is induced in the implantable medical device. On the other hand, when the data stream included a plurality of successive "0"s the power level is reduced. Elevated induced power levels in the implantable medical device may exceed a maximum recommended operating threshold for proper operation of the device, whereas if the power level falls to below a minimum operating threshold then it may be insufficient to power the at least one component. Accordingly, it is desirable to sustain a substantially constant power level induced in the implantable medical device irrespective of the bits in the data stream being transmitted. Another problem previously mentioned with respect to the prior art is possible loss of data during recovery due to improper centering of the demodulated envelope caused by variations in difference in the received power level between the respective high and low bits depending on the coupling distance between the coils of the external and internal devices. This latter disadvantage occurs in all telemetry systems employing conventional binary encoding, regardless of whether the system is a passive telemetry system or not.

In order to overcome these aforementioned shortcomings, prior to transmission to the implantable medical device, the RF communication signal is subject to a DC balanced (zero DC offset) encoding scheme, e.g., a Manchester encoding scheme, by the processor 140 of the external device 100. In a Manchester encoding scheme, rather than being represented as levels, a logic "0" is represented as an upward edge transition from 0 to 1, while a logic "1" is represented as a downward edge transition from 1 to 0. By way of example, the data stream "0101010000000010111111101" when subject to Manchester encoding becomes "01 10 01 10 01 10 01 01 01 01 01 01 01 10 01 10 10 10 10 10 10 01 10".

Employing a DC balanced encoding scheme (e.g., Manchester encoding) having an equal number of "0"s and "1"s prior to transmitting the RF modulated signal from the external device is advantageous in that it: (i) ensures that a substantially constant amount of power is induced in the implantable medical device regardless of the data stream being transmitted; and (ii) facilitates demodulation of the original data signal by properly centering the modulated signal prior to passing through the data slicer. Addressing each advantage in detail, a DC balanced encoding scheme ensures transition between signal levels at the middle of each bit (e.g., rising edge or falling edge to indicate a "0" or "1", respectively) thereby maintaining a substantially constant level (equal to an average power between the high and low bits) of induced power level in the internal device irrespective of the data being transmitted. Furthermore, a DC balanced encoding scheme such as Manchester encoding forces symmetry in the data stream by ensuring the same number of "1"s and "0"s due to the transitions or toggling between states for each bit regardless of the data being sent. DC balancing of the data slicer therefore optimizes the reliability in recovery of the original data stream and thus robustness of transmissions.

FIG. 3 is a graphical representation for an exemplary data bit stream "0101010000000010111111101" showing three waveforms representative of different stages in the RF wireless communication system shown in FIG. 2 including an external device that employs DC balanced encoding in wireless communication with an implantable medical device. As shown in FIG. 3, the use of Manchester encoding forces symmetry in the data stream by ensuring the same number of "1"s and "0"s due to the transitions or toggling between states for each bit regardless of the data being sent. The transitions or toggling between states for each bit ensures that the envelope will be properly centered and symmetrically sliced. As a result, potential loss in recovered data is reduced thereby improving the robustness of transmission. Furthermore, the use of the Manchester encoding prior to transmission from the external device ensures transition between signal levels at the middle of each bit (e.g., rising edge or falling edge to indicate a "0" or "1", respectively) thereby maintaining a substantially constant level (equal to an average power between the high and low bits) of induced power level in the internal device irrespective of the data being transmitted.

In the preferred medical implant application of FIG. 2 including an external device 100 and implantable medical device 105, only the external device has an active emitter producing an RF carrier wave and thus only communications from the external device to the implantable medical device are subject to DC balanced encoding. Since the implantable medical device in the preferred medical implant application does not emit a carrier wave, no Manchester encoding is necessary for RF communication transmitted from the implantable medical device to the external device. However, it is contemplated and within the intended scope of the present invention to employ DC balanced encoding prior to transmission from any device, regardless of whether an external device, internal device or both, that includes an active emitter.

The present invention has been shown and described with respect to a passive telemetry system in a medical application. These same concepts are equally applicable to any passive telemetry system in other fields of endeavor. As has been described above, the use of a DC balanced encoding scheme specifically for a passive telemetry system is advantageous in that it eliminates fluctuations in power induced in the implantable medical device irrespective of the bit stream being transmitted while employing a passive power source. Nevertheless, the present invention of employing a DC balanced encoding scheme in the transmitting device is still advantageous with active telemetry systems in that the RF energy component of the DC balanced encoded RF modulated data signal is itself DC balanced and thus decoding by the slicer is more robust.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A telemetry system comprising:
a first device comprising:
a processor that employs a DC balanced encoding scheme to generate a DC balanced encoded data signal;
a carrier generator for generating an RF carrier wave;
a modulator for modulating the RF carrier wave by the DC balanced encoded data signal and generating a DC balanced encoded RF modulated data signal including DC balanced RF energy; and
a transmitter for wirelessly transmitting the DC balanced encoded RF modulated data signal.

2. The system in accordance with claim 1, wherein the DC balanced encoding scheme is Manchester encoding.

3. The system in accordance with claim 1, wherein the modulator comprises:
a mixer coupled to the processor for modulating the RF carrier wave by the DC balanced encoded data signal; and an amplifier for amplifying the output of the mixer and producing the DC balanced encoded RF modulated data signal.

4. The system in accordance with claim 1, wherein the modulator comprises:
an amplifier for amplifying the DC balanced encoded data signal and producing an amplified DC balanced encoded data signal; and
a mixer coupled to the amplifier for modulating the RF carrier wave by the amplified DC balanced encoded data signal and producing the DC balanced encoded RF modulated data signal.

5. The system in accordance with claim 1, further comprising a second device for receiving the DC balanced encoded RF modulated data signal transmitted by the first device, the DC balanced RF energy eliminating drift in baseline voltage irrespective of data transmission so as to improve recovery of data by the second device.

6. The system in accordance with claim 5, wherein the second device further comprises:
a converter for extracting the DC balanced RF energy from the received DC balanced encoded RF modulated data signal and converting the DC balanced RF energy to a substantially constant average induced voltage, irrespective of data being transmitted, for powering at least one component of the second device.

7. The system in accordance with claim 6, wherein the second device further comprises:
a demodulator for extracting an envelope from the DC balanced encoded RF modulated data signal received by the second device; and
a slicer coupled to the demodulator to receive the extracted envelope and produce a centered, sliced and shaped recovered data.

8. The system in accordance with claim 5, wherein the first device is separated from the second device by a boundary.

9. The system in accordance with claim 8, wherein the first device is an external control device and the second device is an implantable medical device.

10. A telemetry system comprising:
a first device comprising:
a processor that employs a DC balanced encoding scheme to generate a DC balanced encoded data signal;
a carrier generator for generating an RF carrier wave;
a modulator for modulating the RF carrier wave by the DC balanced encoded data signal and generating a DC balanced encoded RF modulated data signal including DC balanced RF energy;
a transmitter for wirelessly transmitting the DC balanced encoded RF modulated data signal; and
a second device receiving the DC balanced encoded RF modulated data signal transmitted by the first device, the DC balanced RF energy eliminating drift in baseline voltage irrespective of data transmission so as to improve recovery of data by the second device.

11. The system in accordance with claim 10, wherein the DC balanced encoding scheme is Manchester encoding.

12. The system in accordance with claim 10, wherein the modulator comprises:
a mixer coupled to the processor for modulating an RF carrier signal with the DC balanced encoded data signal; and
an amplifier for amplifying the output of the mixer and producing the DC balanced encoded RF modulated data signal.

13. The system in accordance with claim 10, wherein the modulator comprises:
an amplifier for amplifying the DC balanced encoded data signal and producing an amplified DC balanced encoded data signal; and
a mixer coupled to the amplifier for modulating the RF carrier wave by the amplified DC balanced encoded data signal and producing the DC balanced encoded RF modulated data signal.

14. The system in accordance with claim 13, wherein the second device comprises a converter for extracting the DC balanced RF energy from the received DC balanced encoded RF modulated data signal and converting the DC balanced RF energy to a substantially constant average induced voltage, irrespective of data being transmitted, for powering at least one component of the second device.

15. The system in accordance with claim 10, wherein the second device comprises:
a demodulator for extracting an envelope from the DC balanced encoded RF modulated data signal received by the second device; and
a slicer coupled to the demodulator to receive the extracted envelope, substantially center the envelope about a reference voltage, slice the envelope substantially symmetric relative to the reference voltage, and reshape the sliced envelope to produced a recovered data stream.

16. The system in accordance with claim 10, wherein the first device is separated from the second device by a boundary.

17. The system in accordance with claim 16, wherein the first device is an external control device and the second device is an implantable medical device.

18. A method for RF communication between a first device and a second device, comprising the steps of:
applying a DC balanced encoding scheme to a data signal to produce a DC balanced encoded data signal;
modulating a generated RF carrier wave by the DC balanced encoded data signal to produce a DC balanced encoded RF modulated data signal including DC balanced RF energy;
wirelessly transmitting the DC balanced encoded RF modulated data signal from the first device; and
receiving at the second device the DC balanced encoded RF modulated data signal, the DC balanced RF energy eliminating drift in baseline voltage irrespective of data transmission so as to improve recovery of data by the second device.

19. The method in accordance with claim 18, further comprising the steps of:
extracting the DC balanced RF energy from the received DC balanced encoded RF modulated data signal;
converting the DC balanced RF energy to a substantially constant average induced voltage irrespective of data being transmitted; and
powering at least one component of the second device using the substantially constant average induced voltage.

20. The method in accordance with claim 18, wherein the first device is an external control device and the second device is an implantable medical device.

* * * * *